United States Patent [19]

Wood et al.

[11] Patent Number: 5,362,484

[45] Date of Patent: Nov. 8, 1994

[54] HAIR CARE COMPOSITION FOR CONDITIONING HAIR WITH SILICONE OIL

[75] Inventors: James L. Wood, Elmhurst; Andrea Mariahazy, Westchester, both of Ill.

[73] Assignee: Alberto-Culver Company, Melrose Park, Ill.

[21] Appl. No.: 86,006

[22] Filed: Jul. 1, 1993

Related U.S. Application Data

[63] Continuation-in-part of Ser. No. 896,161, Jun. 10, 1992, abandoned.

[51] Int. Cl.$^5$ ...................... A61K 7/06; A61K 31/695
[52] U.S. Cl. ...................... 424/70; 514/938; 514/63
[58] Field of Search ............ 424/70, 71; 514/937, 514/938, 941, 63

[56] References Cited

U.S. PATENT DOCUMENTS

| | | | |
|---|---|---|---|
| 4,563,346 | 1/1986 | Deckner | 424/59 |
| 5,143,722 | 9/1992 | Hollenberg | 424/63 |
| 5,216,033 | 6/1993 | Pereira | 424/63 |
| 5,237,035 | 8/1993 | O'Lenick | 528/27 |

OTHER PUBLICATIONS

CTFA International Cosmetic Ingredient Dictionary (1991), p. 377.

*Primary Examiner*—Thurman K. Page
*Assistant Examiner*—Sally Gardner
*Attorney, Agent, or Firm*—Tilton, Fallon, Lungmus & Chestnut

[57] ABSTRACT

A hair care composition for conditioning hair with silicone oil comprisese a stable emulsion of water-insoluble hair conditioning silicone oil dispersed in a liquid carrier composed essentially of polyoxyalkylene glycol and an emulsifier consisting of a silicone phosphate salt in which the anionic moiety comprises a copolymer of dimethylpolysiloxane and polyoxyethylene.

11 Claims, No Drawings

HAIR CARE COMPOSITION FOR CONDITIONING HAIR WITH SILICONE OIL

RELATED APPLICATION

This application is a continuation-in-part of copending application Ser. No. 07/896,161, filed Jun. 10 1992, now abandoned.

FIELD OF INVENTION

The field of this invention is hair treating compositions including hair conditioning emulsions and shampoo emulsions. More particularly, this invention relates to hair care emulsions containing silicone oils.

BACKGROUND OF INVENTION

The term "silicone oil" is used herein to designate water-insoluble silicone polymers which are applied to hair to improve its feel or appearance. Silicone oils can provide the hair with a silky, lubricious feel. They can also provide a lusterization effect. These results are obtained by coating hair strands with thin films of silicone oil. Since silicone oils are substantially water-insoluble, after application to the hair they tend to remain thereon. Silicone oil can therefore be applied in a shampoo, or in a hair conditioner which is applied after shampooing and followed by water-rinsing.

The two most common types of hair conditioning silicone oils are referred to in the International Cosmetic Ingredient Dictionary (CTFA) as "dimethicone" and "dimethiconol". Dimethicone is defined as a mixture of fully methylated linear siloxane polymers end blocked with trimethylsiloxy units. Dimethiconol is a dimethyl silicone polymer terminated with hydroxyl groups. Such hair conditioning silicone oils are relatively non-volatile liquids, which are obtainable from commercial sources in the United States and other countries. For example, silicone fluids are sold by Dow Corning Corporation, Midland, Mich. Among the silicone oils (also called fluids) supplied by Dow Corning for use in hair treating compositions is a solution of high-viscosity dimethiconol fluid in dimethicone (Dow Corning Q2-1403 Fluid).

Since silicone oils have limited solubility in water and other polar solvents, they are usually applied in the form of dispersions or emulsions. For example, in a water-based shampoo or hair conditioner, the silicone oil may be dispersed with the aid of an emulsifying agent, and the dispersion or emulsion may be stabilized by the inclusion of thickeners.

Cationic hair conditioning agents are commonly used in hair conditioning compositions, and to a lesser extent in shampoo formulations. Typically, cationic hair conditioning agents contain one or more cationic quaternary nitrogen or amido amine groups, and one or more hydrophobic long chain aliphatic or silicone polymers. The cationic group can provide a degree of substantivity between the conditioning agent and hair. The long chain hydrophobic groups, which are derived from long chain fatty acids or are silicone polymers, can provide hair conditioning or hair repair functions.

The published European patent application 0 115 806 describes a hair conditioning composition containing silicone oil dispersed in water. The composition also contains dimethicone copolyol, which the Cosmetic Dictionary defines as a polymer of dimethylpolysiloxane with polyoxyethylene and/or polyoxypropylene side chains. To provide a stable emulsion, the composition is in the form of a gel vehicle, consisting of a lipid material and a cationic surfactant.

The incorporation of cationic hair conditioners in anionic surfactant-based shampoos presents a stability problem because of the tendency of the conditioner to interact with the surfactant. Anionic-cationic complexing of these ingredients can result in an unstable dispersion. The complexed conditioner/surfactant may settle out of the dispersion. However, some formulations have been developed in which quaternary nitrogen-containing conditioning agents are incorporated in anionic surfactant shampoos. U.S. Pat. Nos. 4,704,272, 3,964,500, and 5,034,218 are illustrative of such formulations. As described in these patents, the shampoo formulations may also include silicone oil which is dispersed and maintained in suspension by the inclusion of thickeners.

In the cited U.S. Pat. No. 4,704,272, a tri (long-chain) alkyl quaternary ammonium salt or a tri (long-chain) amine is utilized in combination with a synthetic anionic surfactant, a silicone oil, and a suspending or thickening agent. The patent disclosure indicates that the cationic conditioner does not interact with the anionic surfactant. Silicone oils are also used in after-shampoo hair conditioning emulsions. (See, for example, U.S. Pat. No. 4,387,090.)

As far as it is known, silicone polymers having an anionic functional group such as a phosphate have not heretofore been used commercially in hair conditioning compositions. However, methods of preparation and the chemical structure of phosphated silicone polymers are disclosed in U.S. Pat. No. 5,070,171. The base polymer described in these patents contains a dimethylpolysiloxane chain with a side chain of polyoxyalkylene. This structure can be regarded as a co-polymer of a siloxane chain and a polyoxyalkylene chain.

This type of silicone co-polymers is designated by the CTFA as "dimethicone copolyol". The Cosmetic Dictionary definition is: a polymer of dimethylpolysiloxane with polyoxyethylene and/or polyoxypropylene side chains. Using that terminology, the phosphated silicone polymers of the above-cited patent can be called dimethicone copolyol phosphates. In terms of chemical structure, the phosphate group forms the terminus of the polyoxyalkylene side chain, and the end hydroxyl has been converted to an ester linkage to the phosphate group.

Hair conditioning lotions are conventionally formulated as aqueous solutions, dispersions or emulsions. Organic solvents are not ordinarily used as carriers for the hair treating agents. Organic liquids may be included in the total formula as emulsifiers or hair conditioners. For example, U.S. Pat. No. 4,493,824 describes a water-based hair rinse containing a minor amount of polyethylene glycol.

SUMMARY OF INVENTION

The liquid hair care composition of the invention comprises a novel formulation for conditioning hair with silicone oil. The emulsifier is a fatty quaternary amine salt or a fatty amido amine salt of a dimethicone copolyol phosphate. These cationic salts contain at least one basic nitrogen group and at least one alkyl or alkylene group of 8 to 22 carbons, such as the aliphatic groups derived from long chain fatty acids. The dimethicone copolyol phosphate which forms the salt contains siloxane and oxyethylene chain of defined and limited lengths which cooperate to provide a hydrophobic-hydrophilic balance. More specifically, a siloxane chain of 20 to 40 dimethylsiloxy units and an oxyethylene chain of 3 to 15 oxyethylene units are provided. This emulsifier salt has particular application to the preparation of a hair care emulsion containing silicone oils. A further discovery is that that emulsion's stability can be enhanced by using a polyoxyalkylene glycol carrier for the silicone oil and the emulsifier salt. A significant amount of the emulsifier salt is employed to form a stable emulsion of the silicone oil in the glycol.

DETAILED DESCRIPTION

The base material for preparing the emulsifier salts of this invention comprise a copolymer of dimethylpolysiloxane and polyoxyethylene which terminates in an anionic phosphate. Such dimethicone copolyol phosphates can be prepared as described in U.S. Pat. No. 5,070,171, or they can be obtained commercially from Phoenix Chemical, Inc., Somerville, N.J., and/or Siltech, Inc., Norcross, Ga. Phoenix Chemical sells dimethicone copolyol phosphates under its trademark "Pecosil".

For use in the emulsifier system of this invention, the siloxane chain is believed to function as a hydrophobic component while the oxyethylene chain functions as a hydrophilic component. The hydrophobic-hydrophilic balance between these chains is of importance in achieving a high level of emulsifier activity. A desirable balance is obtained when the siloxane chain contains from 20 to 40 dimethylsiloxane units and the oxyethylene chain contains from 3 to 15 oxyethylene units. In a preferred embodiment, the siloxane chain has from 25 to 35 dimethylsiloxane units, and the oxyethylene chain has from 4 to 10 oxyethylene units. These ranges refer to average or representative chain lengths. It will be understood that not all of the co-polymer molecules will have identical chain lengths.

A representative commercial product which can be used for preparing an emulsifier salt for use in this invention is sold by Phoenix Chemical as "Pecosil PS-100". It is estimated that the siloxane chain of this product contains on the average of about 32 dimethylsiloxane units and that the oxyethylene chain contains on the average about 7 oxyethylene units. The oxyethylene chain terminates in an ester-linked phosphate group.

The phosphate group should be in free acid form for conversion to the fatty amine or fatty amido amine salts. The following formulas I and II are representative of the fatty amine and amido amine salts of the dimethicone copolyol phosphates. As described in U.S. Pat. 5,070,171 (see col. 5, lines 40-54), the dimethicone copolyol phosphates may be mono-esters or di-esters, and are typically prepared and used as a mixture of the mono- and di-esters. Formula I represents the mono-ester form and formula II the di-ester form.

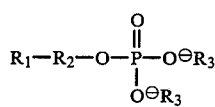

I.

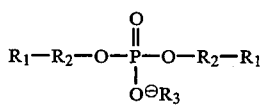

II.

In the foregoing formulas $R_1$, represents the dimethylpolysiloxane polymer, and $R_2$ the polyoxyethylene chain which are connected by ester oxygens to the phosphorus atom. The letter $R_3$ represents the cationic moiety which contains at least one cationic nitrogen group and at least one long chain aliphatic (alkyl or alkylene) group. In some embodiments, the siloxane polymer may have multiple side chains of polyoxyethylene. If such compounds are employed for the purpose of this invention, the total of the oxyethylene units should correspond with the ranges set out above. The oxyethylene chains may be either linear or branched with reference to the siloxane polymer portion of the molecule.

The cationic moiety, which contains at least one and preferably not more than three cationic quaternary nitrogen or amido amine groups, also contains at least one and preferably not more than two alkyl or alkylene chains of 8 to 22 carbons. Fatty quaternary amine compounds are particularly desirable. The term "fatty" designates alkyl or alkylene residues of fatty acids. Fatty quaternary amines or fatty amido amine in dimer form can be used, thereby providing a two long chain fatty groups and two amine or amido amine groups. For example, such compounds may contain an aliphatic chain of up to 36 carbons.

The amine and amido amine salts of the silicone phosphate compounds can be prepared as described in U.S. Pat. No. 5,093,452. These can be obtained from Phoenix Chemical, Inc., Somerville, N.J. and Siltech, Inc., Norcross, Ga. One of the starting materials for the reaction, a silicone phosphate ester, can be prepared as described in U.S. Pat. No. 5,070,171 incorporated herein by reference, and are also available from Phoenix Chemical, Inc. and Siltech, Inc. Fatty quaternary or fatty amido amine compounds which can be used to convert the silicone phosphate esters to the desired salts can be obtained from commercial sources. These include Phoenix Chemical, Inc., Somervile, N.J., or Croda, Inc., New York, N.Y., Inolex Chemical Co., Philadelphia, Pa., Scher Chemicals, Inc., Clifton, N.J. and others.

With reference to the cationic moiety of the salts used in practicing the invention. $R_3$ can be represented as:

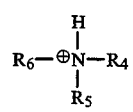

III.

wherein $R_4$ is $C_8$ to $C_{22}$ aliphatic (alkyl or alkylene), and $R_5$ and $R_6$ are H, or $C_8$ to $C_{22}$ aliphatic (alkyl or alkylene).

In another embodiment, $R_3$ can be represented as:

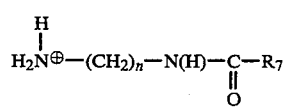

IV.

wherein n is an integer from 1 to 22, and $R_7$ is $C_8$ to $C_{22}$ aliphatic (alkyl or alkylene) or an alkylene dimer thereof.

Water-insoluble, non-volatile silicone oils (sometimes called silicone fluids) are well known in the cosmetic arts, and are available through a number of commercial sources in the United States and other countries. They are extensively described in the patent literature. For example, reference may be had to U.S. Pat. No.

4,704,272, and the description of non-volatile silicone fluids found in columns 4 and 5 thereof. Such silicone oils or fluids can be obtained in the United States from the Dow Corning Corporation, Midland, Mich., and other companies such as Siltech, Inc., Norcross, Ga. A particularly suitable product is Dow Corning Q2-1403 Fluid, which is a solution of high-viscosity dimethiconol fluid and dimethicone.

In complete hair conditioner formulations, water-dispersible or water-soluble silicone polymers can also be used. For example, dimethicone copolyols may be used as auxiliary ingredients. Representative examples are Dow Corning 193 surfactant and Siltech "Silwax WS".

For the purpose of preparing stable emulsions using the emulsifier system of this invention for incorporation of silicone oils in hair conditioners, the liquid carrier is a polar solvent such as water, polyoxyalkylene glycol and lower alkyl alcohols among others. For example, a preferred carrier is alcohols, among others. In particular, polyoxyethylene glycol carriers are desirable. Alternatively, the carrier may comprise a copolymer of polyoxyethylene and polyoxypropylene. Polyoxyethylene liquids suitable for use in complete formulations of this invention are available from Phoenix Chemical, Inc., Somerville, N.J., under the trademark name "Phoenoxide". A suitable example is "Phoenoxide E-400". Similar products are available from Union Carbide Corp., Danbury, Conn., under the trademark name "Carbowax". In the Cosmetic Dictionary, they are referred to by the initials "PEG", for example, PEG-8 corresponds with "Phoenoxide E-400". That product has an average molecular weight of about 400. While polyoxyethylene products are available in molecular weights from 200 to 20,000, for purpose of the present invention, lower molecular weight products are preferred which have molecular weights in the range from 200 to 600. Instead of a polyoxyethylene carrier, carriers composed of polyoxyethylene chain in combination with polyoxypropylene chains can be used. These products are available from BASF Wyandotte Corp., Parsippany, N.J., under the trademark name "Pluronics". The particular polyoxyalkylene carrier selected will depend on the desired viscosity of the complete composition. When a relatively low molecular weight carrier is selected, the viscosity may be increased and a thickening action obtained by using it in admixture with a polyoxyalkylene liquid of higher viscosity. For example, when the primary carrier is PEG-8, PEG-350 may be used as a thickener, being a product obtainable from Union Carbide as "Carbowax 20M".

As it is well known in the cosmetic arts, complete formulations may also include other compounds which have desirable hair conditioning properties. For example, AMP-isostearoyl hydrolyzed soy protein can be used. The product is defined in the Cosmetic Dictionary as the aminomethylpropanol salt of the condensation product of isostearic acid chloride with hydrolyzed soy protein. It is available from Kato Worldwide, Ltd., Mount Vernon, N.Y., as Natural Blend 23.

PRACTICE OF INVENTION

In practical uses of the silicone oil emulsifier of this invention, the silicone phosphate salt, as described above, can be combined with the silicone fluid to form a dispersion for addition to a complete hair care conditioner. Alternatively, the silicone phosphate salt can be introduced into a polar carrier, such as a polyoxyethylene glycol carrier, and the silicone oil emulsified therein, and other soluble or dispersible ingredients added to produce a complete hair conditioner formulation.

For complete formulations on a percent by weight basis from 1 to 10% of silicone oil can be used together with 1 to 10% of the silicone phosphate salt emulsifier. The quantity of silicone oil should not exceed the amount for which a stable emulsion is obtained. On a total formula basis, preferred amounts of silicone oil are in the range from about 3 to 7 parts by weight per hundred parts of the conditioning formulation. The corresponding amount of the emulsifier is from 3 to 7 parts per 100 parts of the conditioning formulation.

The polyoxyalkylene glycol carrier preferably is the major component of the formulation. For example, the complete formulation may contain from 60 to 90–98 parts by weight of the carrier per hundred parts of formulation.

A representative generalized formula for preparing a hair conditioning emulsion in accordance with the present invention is set out below.

| General Formula | |
|---|---|
| Ingredients | Parts by Wt. |
| Silicone Phosphate Salt[a] | 1–10 |
| Silicone Oil[b] | 1–10 |
| PEG Carrier[c] | 60–98 |

[a] Fatty quaternary amine or fatty amido amine salt of dimethicone copolyol phosphate.
[b] Water-insoluble non-volatile dimethicone and/or dimethicone and/or dimethiconol polymer.
[c] Polyoxyethylene glycol of MW 200–20,000.

The following examples provide further information for practicing the invention.

EXAMPLE I

A silicone phosphate salt was prepared from a dimethicone copolyol phosphate having a structure corresponding to Phoenix Chemical Pecosil PS-100 and myristamidopropyl dimethylamine, The procedure used was as follows:

| Materials | Quantity |
|---|---|
| Myristamidopropyl Dimethylamine (Phoenix Chemical Catemol 140) | 8 pounds |
| Dimethicone Copolyol Phosphate (Phoenix Chemical Pecosil PS-100) | 67.0 pounds |
| Water | 25.0 pounds |

Procedure

To a suitable mixing vessel add 8.0 pounds of myristamidopropyl dimethylamine. Next, add 67.0 pounds of dimethicone copolyol phosphate with vigorous stirring. Stir for 10 minutes to a white uniform paste. Next, add 25.0 pounds of water. Stir until product becomes clear.

EXAMPLE II

Following procedures similar to Example 1, dimeramidopropyl dimethylamine dimethicone copolyol phosphate was prepared. Materials used and the procedure were as follows.

| Materials | Quantity |
|---|---|
| Dimethicone Copolyol Phosphate (Phoenix Chemical Pecosil PS-100) | 60.0 pounds |

-continued

| Materials | Quantity |
| --- | --- |
| Dimeramidopropyl Dimethylamine (Phoenix Chemical Catemol 360) | 10.0 pounds |
| Propylene Glycol | 30.0 pounds |

Procedure

To a suitable mixing vessel is 60.0 pounds of dimethicone copolyol phosphate. Next, add dimeramidopropyl dimethylamine with vigorous stirring. Mix for 10 minutes to a white uniform paste. Next, add 30.0 pounds of propylene glycol. Stir until products becomes clear.

EXAMPLE III

A complete hair conditioner is prepared by mixing together the following ingredients in the proportions shown.

| No. | Ingredients | Weight Percent |
| --- | --- | --- |
| 1 | PEG-8 (Phoenix Chemical Phoenoxide E-400) | 70.5 |
| 2 | Hydroxypropylcellulose | 1.0 |
| 3 | PEG-350 (Union Carbide Carbowax 20M) | 3.0 |
| 4 | Dilinolamidopropyl Dimethylamine Dimethicone Copolyol Phosphate (and) Propylene Glycol (Phoenix Chemical Dicopamine DP) | 5.0 |
| 5 | Dimethicone (and) Dimethiconol (Dow Corning Fluid Q2-1403) | 5.0 |
| 6 | Quaternium-80 (Siltech Silquat Q100) | 5.0 |
| 7 | Dimethicone Copolyol (Siltech MFF 159-100) | 5.0 |
| 8 | Dimethicone Copolyol (Siltech Silwax WS) | 5.0 |
| 9 | AMP-Isostearoyl Hydrolyzed Wheat Protein (and) etc. (Kato Natural Blend #23) | 0.5 |

The foregoing ingredients can be combined as follows.

Step 1: Add Item #1 PEG-8 to main tank. While stirring rapidly, add Item #2 hydroxypropylcellulose and begin heating to 190° F for 3 hours or until Item #2 is entirely dissolved. Begin cooling to 160° F.

Step 2: When main tank has reached a temperature of 160° F., add Item #3 PEG-350 and Item #4 dilinolamidopropyl dimethylamine dimethicone copolyol phosphate (and) propylene glycol. Maintain temperature at 160° F. and stir rapidly for 30 minutes or until Item #3 is completely dissolved.

Step 3: Add Item #5 dimethicone (and) dimethiconol. Maintain at 160° F. and stir rapidly for 30 minutes.

Step 4: Add Item #6 quaternium-80, Item #7 dimethicone copolyol, Item #8 dimethicone copolyol (previously melted). Maintain at 160° F. and stir rapidly for 30 minutes. Check batch to make sure product is well blended and entirely homogeneous in appearance.

Step 5: While continuing to stir rapidly, begin cooling very slowly at a rate that does not exceed 10 degrees Farenheit per 30 minutes.

Step 6: At 100° F., add Item #9 AMP-isostearoyl hydrolyzed wheat protein (and) etc. Continue stirring rapidly and cooling slowly as in Step 5. At 85° F., stop cooling and stirring.

EXAMPLE IV

A complete hair conditioner is prepared by mixing together the following ingredients in the proportions shown.

| No. | Ingredients | Weight Percent |
| --- | --- | --- |
| 1 | PEG-8 (Phoenix Chemical Phoenoxide E-400) | 70.5 |
| 2 | Hydroxypropylcellulose | 1.0 |
| 3 | PEG-350 (Union Carbide Carbowax 20M) | 3.0 |
| 4 | Myristamidopropyl Dimethylamine Dimethicone Copolyol Phosphate (and) Propylene Glycol (Phoenix Chemical Dicopamine MP) | 5.0 |
| 5 | Dimethicone (and) Dimethiconol (Dow Corning Fluid Q2-1403) | 5.0 |
| 6 | Quaternium-80 (Siltech Silquat Q100) | 5.0 |
| 7 | Dimethicone Copolyol (Siltech MFF 159-100) | 5.0 |
| 8 | Dimethicone Copolyol (Siltech Silwax WS) | 5.0 |
| 9 | AMP-Isostearoyl Hydrolyzed Wheat Protein (and) etc. (Kato Natural Blend #23) | 0.5 |

The foregoing ingredients can be combined as follows.

Step 1: Add Item #1 PEG-8 to main tank. While stirring rapidly, add Item #2 hydroxypropylcellulose and begin heating to 190° F. Continue stirring rapidly at 190° F. for 3 hours or until Item #2 is entirely dissolved. Begin cooling to 160° F.

Step 2: When main tank has reached a temperature of 160° F., add Item #3 PEG-350 and Item #4 myristamidopropyl dimethicone copolyol phosphate (and) propylene glycol. Maintain temperature at 160° F. and stir rapidly for 30 minutes or until Item #3 is completely dissolved.

Step 3: Add Item #5 dimethicone (and) dimethiconol. Maintain at 160° F. and stir rapidly for 30 minutes.

Step 4: Add Item #6 quaternium-80, Item #7 dimethicone copolyol, Item #8 dimethicone copolyol (previously melted). Maintain at 160° F. and stir rapidly for 30 minutes. Check batch to make sure product is well blended and entirely homogeneous in appearance.

Step 5: While continuing to stir rapidly, begin cooling very slowly at a rate that does not exceed 10 degrees Farenheit per 30 minutes.

Step 6: At 100° F., add Item #9 AMP-isostearoyl hydrolyzed wheat protein (and) etc. Continue stirring rapidly and cooling slowly as in Step 5. At 85° F., stop cooling and stirring.

We claim:

1. A liquid hair care composition for conditioning hair with silicone oil, comprising a stable emulsion of a water-insoluble hair conditioning non-volatile silicone oil dispersed in a liquid carrier consisting of polyoxyalkylene glycol selected from polyoxyethylene and copolymers of polyoxyethylene and polyoxypropylene, from 60 to 98 parts by weight of said glycol carrier being present per 100 parts of said composition, and said composition further containing an emulsifier consisting of a silicone phosphate salt having an anionic moiety comprising a copolymer of dimethylpolysiloxane and polyoxyethylene, said salt having a siloxane chain containing from 20 to 40 dimethylsiloxy units, an oxyethylene chain containing from 3 to 15 oxyethylene units, and terminating in an anionic phosphate group, said salt also having a cationic moiety comprising an aliphatic amine or amido amine containing at least one basic nitrogen group and at least one alkyl or alkylene group containing from 8 to 36 carbons said salt being present in an effective amount for emulsifying said non-volatile silicone oil in said glycol carrier.

2. The hair conditioning composition of claim 1 in which said carrier is polyoxyethylene glycol.

3. The hair conditioning composition of claim 1 in which said carrier is a copolymer of polyoxyethylene and polyoxypropylene.

4. The composition of claim 1 in which said silicone oil is a dimethylpolysiloxane polymer.

5. The composition of claim 1 in which said cationic moiety is a fatty amine containing one nitrogen group and one alkyl or alkylene group of from 12 to 22 carbons.

6. The composition of claim 1 in which said cationic moiety is a fatty amido amine containing at least one amido amine group and at least one alkyl or alkylene group of 12 to 22 carbons.

7. The composition of claim 1 in which said siloxane chain contains from 25 to 35 dimethylsiloxy units and said oxyethylene chain contains from 4 to 10 oxyethylene units.

8. A liquid hair care composition for conditioning hair with silicone oil, comprising a stable emulsion of a water-insoluble hair conditioning non-volatile silicone oil dispersed in a liquid carrier consisting of polyoxyethylene glycol selected from polyoxyethylene and copolymers of polyoxyethylene and polyoxypropylene, and said composition further containing an emulsifier consisting of a silicone phosphate salt having an anionic moiety comprising a copolymer of dimethylpolysiloxane and polyoxyethylene, said salt also having a siloxane chain containing from 25 to 35 dimethylsiloxy units, an oxyethylene chain containing from 4 to 10 oxyethylene units, and terminating in an anionic phosphate group, said salt having a cationic moiety comprising an aliphatic amine or amido amine containing at least one basic nitrogen group and at least one alkyl or alkylene group containing from 8 to 36 carbons, said composition containing from 60 to 90 parts by weight of said polyoxyethylene glycol per 100 parts of said composition said salt being present in an effective amount for emulsifying said non-volatile silicone oil in said glycol carrier.

9. The hair care composition of claim 8 in which said silicone oil is a dimethylpolysiloxane polymer.

10. The composition of claim 8 in which said cationic moiety is a fatty amine containing one nitrogen group and one alkyl or alkylene group of from 12 to 22 carbons.

11. The composition of claim 8 in which said cationic moiety is a fatty amido amine containing at least one amido amine group and at least one alkyl or alkylene group of 12 to 22 carbons.

* * * * *

UNITED STATES PATENT AND TRADEMARK OFFICE
CERTIFICATE OF CORRECTION

PATENT NO. : 5,362,484
DATED : November 8, 1994
INVENTOR(S) : Wood, et. al.

It is certified that error appears in the above-indentified patent and that said Letters Patent is hereby corrected as shown below:

Column 9, line 7, claim 1, after "carbons" insert -- "," --.

Column 10, lines 16 and 17, claim 8, after "composition" insert -- , --.

Signed and Sealed this

Seventh Day of March, 1995

*Attest:*

BRUCE LEHMAN

*Attesting Officer*   *Commissioner of Patents and Trademarks*